United States Patent
Williams et al.

(10) Patent No.: US 10,973,544 B2
(45) Date of Patent: Apr. 13, 2021

(54) RETAINING MECHANISM FOR TROCAR ASSEMBLY

(71) Applicant: Covidien LP, Mansfield, MA (US)

(72) Inventors: Justin Williams, Southbury, CT (US); Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 239 days.

(21) Appl. No.: 16/149,291

(22) Filed: Oct. 2, 2018

(65) Prior Publication Data

US 2020/0100808 A1 Apr. 2, 2020

(51) Int. Cl.
| | |
|---|---|
| *A61B 17/34* | (2006.01) |
| *A61B 17/00* | (2006.01) |
| *A61B 17/072* | (2006.01) |
| *A61B 17/115* | (2006.01) |
| *A61B 90/00* | (2016.01) |

(52) U.S. Cl.
CPC ............ *A61B 17/34* (2013.01); *A61B 17/072* (2013.01); *A61B 17/1155* (2013.01); *A61B 2017/0046* (2013.01); *A61B 2017/00486* (2013.01); *A61B 2017/347* (2013.01); *A61B 2090/0813* (2016.02)

(58) Field of Classification Search
CPC ... A61B 17/072; A61B 17/34; A61B 17/1155; A61B 2090/0813; A61B 2017/0046; A61B 2017/00486; A61B 217/347; A61B 2017/00477; A61B 2017/00473
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Jan. 30, 2020, issued in EP Appln. No. 19200764, 6 pages.

*Primary Examiner* — Katherine H Schwiker
*Assistant Examiner* — Raihan R Khandker
(74) *Attorney, Agent, or Firm* — Carter, DeLuca & Farrell LLP (57) ABSTRACT

An adapter assembly for connecting a loading unit to a handle assembly is provided. The adapter assembly includes a sleeve, a trocar assembly releasably securable with the sleeve, and a retaining mechanism configured to releasably secure the trocar assembly within the sleeve and to facilitate cleaning and sterilizing of the adapter assembly.

20 Claims, 9 Drawing Sheets

(56) References Cited

U.S. PATENT DOCUMENTS

| | | |
|---|---|---|
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |

(56) References Cited

U.S. PATENT DOCUMENTS

| | | |
|---|---|---|
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |

(56) References Cited

U.S. PATENT DOCUMENTS

| | | |
|---|---|---|
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |

(56) References Cited

U.S. PATENT DOCUMENTS

| | | |
|---|---|---|
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0235789 A1* | 8/2015 | Calderoni ............ A61B 17/00 200/315 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0296234 A1* | 10/2016 | Richard ................ A61B 17/34 |
| 2016/0302792 A1 | 10/2016 | Motai |
| 2017/0196566 A1* | 7/2017 | Sgroi .................... A61B 17/34 |
| 2017/0224345 A1 | 8/2017 | Cabrera et al. |
| 2017/0333077 A1* | 11/2017 | Williams .............. A61B 17/34 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3146905 A1 | 3/2017 |
| EP | 3192462 A1 | 7/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 8006085 A1 | 6/1990 |
| WO | 98/35614 A1 | 8/1998 |
| WO | 0154594 A1 | 8/2001 |
| WO | 2008107918 A1 | 9/2008 |

* cited by examiner

RETAINING MECHANISM FOR TROCAR ASSEMBLY

BACKGROUND

Technical Field

The present disclosure relates to reusable adapter assemblies for surgical stapling devices. More particularly, the present disclosure relates to a retaining mechanism for releasably securing a removable trocar assembly within a reusable adapter assembly.

Background of Related Art

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly.

Circular stapling devices typically includes a trocar assembly for positioning an attached anvil assembly. The trocar assembly may be releasably securable within the adapter assembly to permit cleaning and sterilizing and reuse of the adapter assembly. It would be beneficial to have a retaining mechanism for releasably securing the trocar assembly with the adapter assembly.

SUMMARY

An adapter assembly for connecting a loading unit to a handle assembly is provided. The adapter assembly includes an outer sleeve, a trocar assembly releasably securable with the outer sleeve, and a retaining mechanism configured to releasably secure the trocar assembly within the outer sleeve. The trocar assembly includes a trocar housing defining first and second openings. The retaining mechanism includes first and second button members configured for operable engagement by a user. The first and second button members are movable between a lock position with the first and second button members being flush with an outer surface of the outer sleeve, a release position in which the first and second button members are recessed below the outer surface of the outer sleeve, and a cleanse position in which the first and second button members extend beyond the outer surface of the outer sleeve. The trocar assembly is securely coupled within the outer sleeve in the lock position.

In embodiments, the retaining mechanism may further include first and second plunger members in operable engagement with the respective first and second button members such that movement of the first button member results in corresponding movement of the first plunger member and movement of the second button member results in corresponding movement of the second plunger member. Each of the first and second plunger members includes a flange portion configured for selective reception within the respective first and second openings of the trocar housing.

The retaining mechanism may further include first and second spring members for biasing the respective first and second plunger members towards each other. The first and second plunger members are spaced apart when the first and second button members are in the lock position. The first and second plunger members may engage the trocar housing when the first and second button members are in the release position. The first and second plunger members may be spaced from the trocar assembly when the first and second button members are in the release position.

Each of the first and second button members of the retaining mechanism may include a pair of tab portions. The tab portions may be configured to engage the outer sleeve to retain the first and second button members within the adapter assembly. The adapter assembly may further include a connector housing for releasably securing a loading unit to the outer sleeve. The trocar assembly may include a trocar member selectively extendable from the trocar housing.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the presently disclosed adapter assembly including a retaining mechanism for securing a removable trocar assembly therein will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 1:
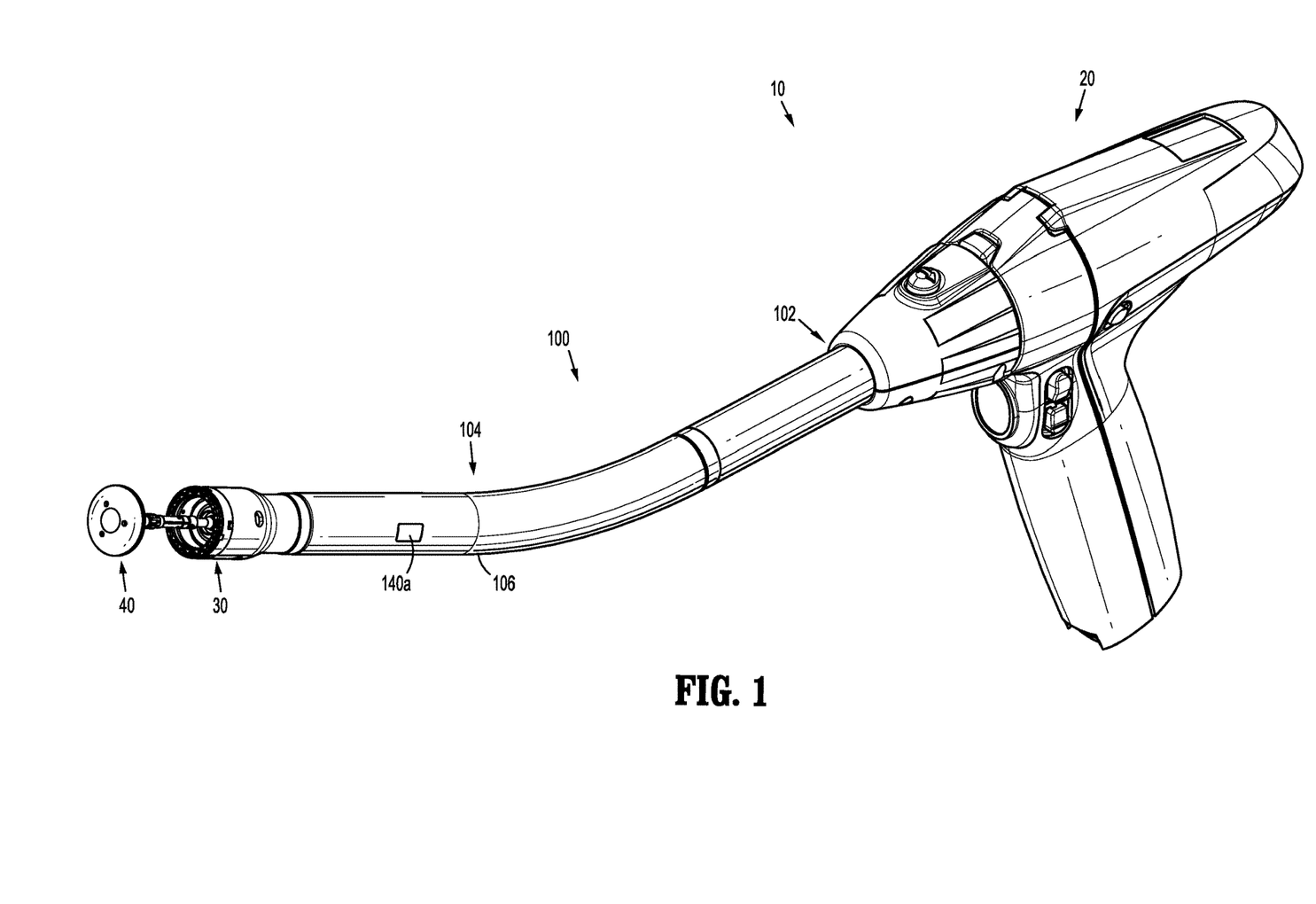
FIG. 1 is a perspective view of a surgical stapling device including an handle assembly and an adapter assembly according to an embodiment of the present disclosure.

Referring initially to FIG. 1, an adapter assembly according to an embodiment of the present disclosure, shown generally as adapter assembly 100, is a component of a surgical stapling device 10. The surgical stapling device 10 further includes a powered handle assembly 20, a loading unit 30, and an anvil assembly 40. Although shown and described with reference to surgical stapling device 10, the aspects of the present disclosure may be modified for use with manual surgical stapling devices having various configurations, and with powered surgical stapling devices having alternative configurations. For a detailed description of exemplary surgical stapling devices, please refer to commonly owned U.S. Pat. No. 9,023,014 ("the '014 patent) and U.S. Pat. Appl. Publ. No. 2012/0253329 ("the '329 application"), the content of each of which is incorporated by reference herein in their entirety.

Figure 2:
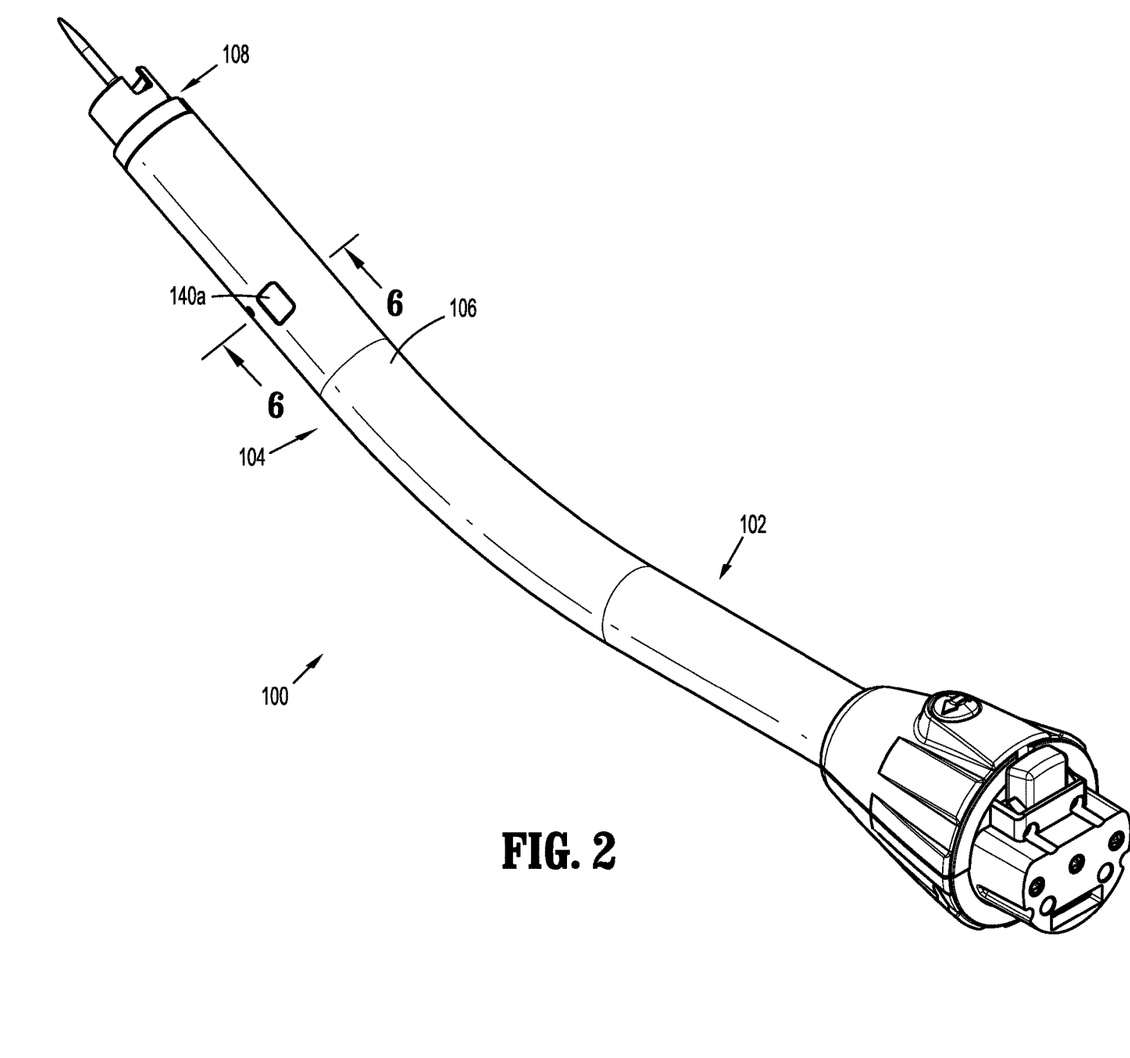
FIG. 2 is a perspective view of the adapter assembly shown in FIG. 1 with a removable trocar assembly extending from a distal portion of the adapter assembly.

With reference to FIG. 2, the adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the present disclosure. For a detailed description of an exemplary adapter assembly, please refer to commonly owned U.S. Pat. App. Pub. No. 2016/0106406 ("the '406 Publication"), the content of which is incorporated by reference herein in its entirety.

Figure 3:
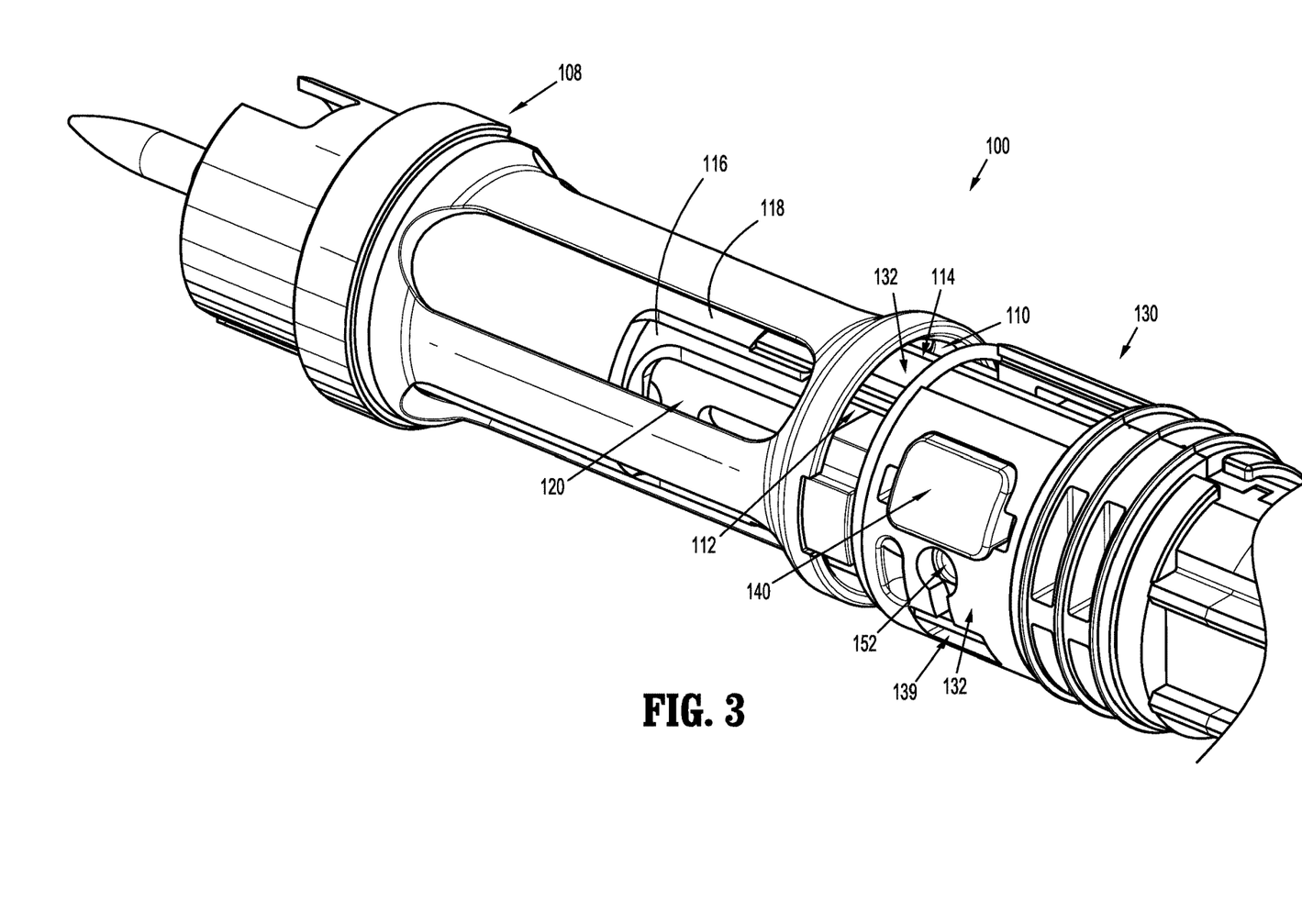
FIG. 3 is a perspective view of the distal portion of the adapter assembly with an outer sleeve removed to expose a retaining mechanism.

With additional reference to FIG. 3, the adapter assembly 100 includes an outer sleeve 106 (FIG. 2), and a connector housing 108 secured to a distal end of the outer sleeve 106. The connector housing 108 is configured to releasably secured an end effector, e.g., the end effector 30 (FIG. 1), to the adapter assembly 100.

Figure 7:
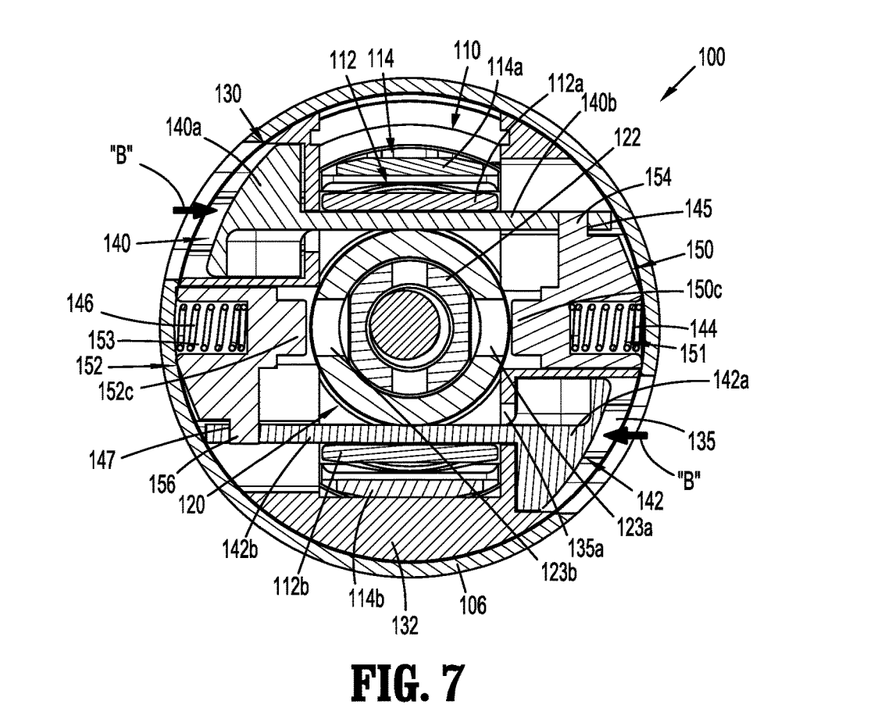
FIG. 7 is the cross-sectional end view of the adapter assembly shown in FIG. 6, with the retainer mechanism in a release position.

A drive assembly 110 (FIG. 3) extends through the outer sleeve 106 (FIG. 2) of the adapter assembly 100, and includes an inner flexible band assembly 112 and an outer flexible band assembly 114. The inner flexible band assembly 112 includes first and second flexible bands 112a, 112b (FIG. 7), and an inner pusher member 116 (FIG. 3) connected to the distal ends of the first and second flexible bands 112a, 112b (FIG. 7). Similarly, the outer flexible band assembly 114 includes first and second flexible bands 114a, 114b (FIG. 7), and an outer pusher member 118. For a detailed description of the structure and function of an exemplary drive assembly, please refer to the '406 Publication, the content of which was previously incorporated herein by reference in its entirety.

Figure 4:
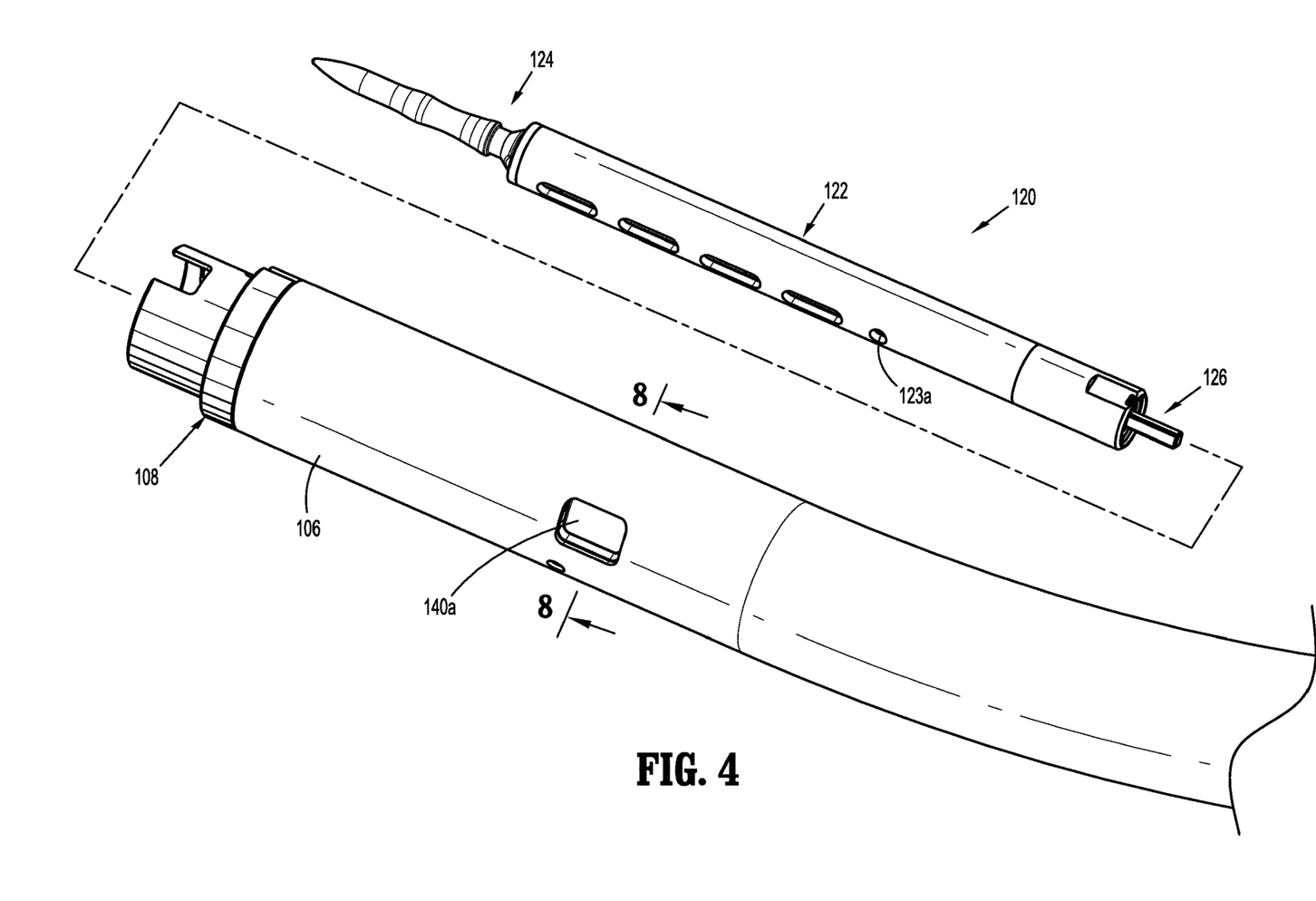
FIG. 4 is a side perspective view of the removable trocar assembly and distal portion of the adapter assembly shown in FIG. 2, with the removable trocar removed from within the adapter assembly.

With additional reference to FIG. 4, the adapter assembly 100 further includes a trocar assembly 120, and a retaining mechanism 130 (FIG. 3) releasably securing the trocar assembly 120 relative to the outer sleeve 106 (FIG. 4) of the adapter assembly 100. The trocar assembly 120 will only be described to the extent necessary to describe the aspects of the present disclosure. For a detail description of the structure and function of an exemplary trocar assembly, please refer to the '406 Publication, the content of which was previously incorporated by reference herein in its entirety.

With particular reference to FIG. 4, the trocar assembly 120 of the adapter assembly 100 (FIG. 2) includes a trocar housing 122, a trocar member 124 slidably disposed within the trocar housing 122, and a drive screw 126 operably received within the trocar member 124 for axially moving the trocar member 124 relative to the trocar housing 122. The trocar housing 122 defines first and second locking openings 123a, 123b (FIG. 7) for receiving respective flange portions 150c, 152c of first and second plunger members 150, 152 (FIG. 7) of a retaining mechanism 130 of the adapter assembly 100.

Figure 5:
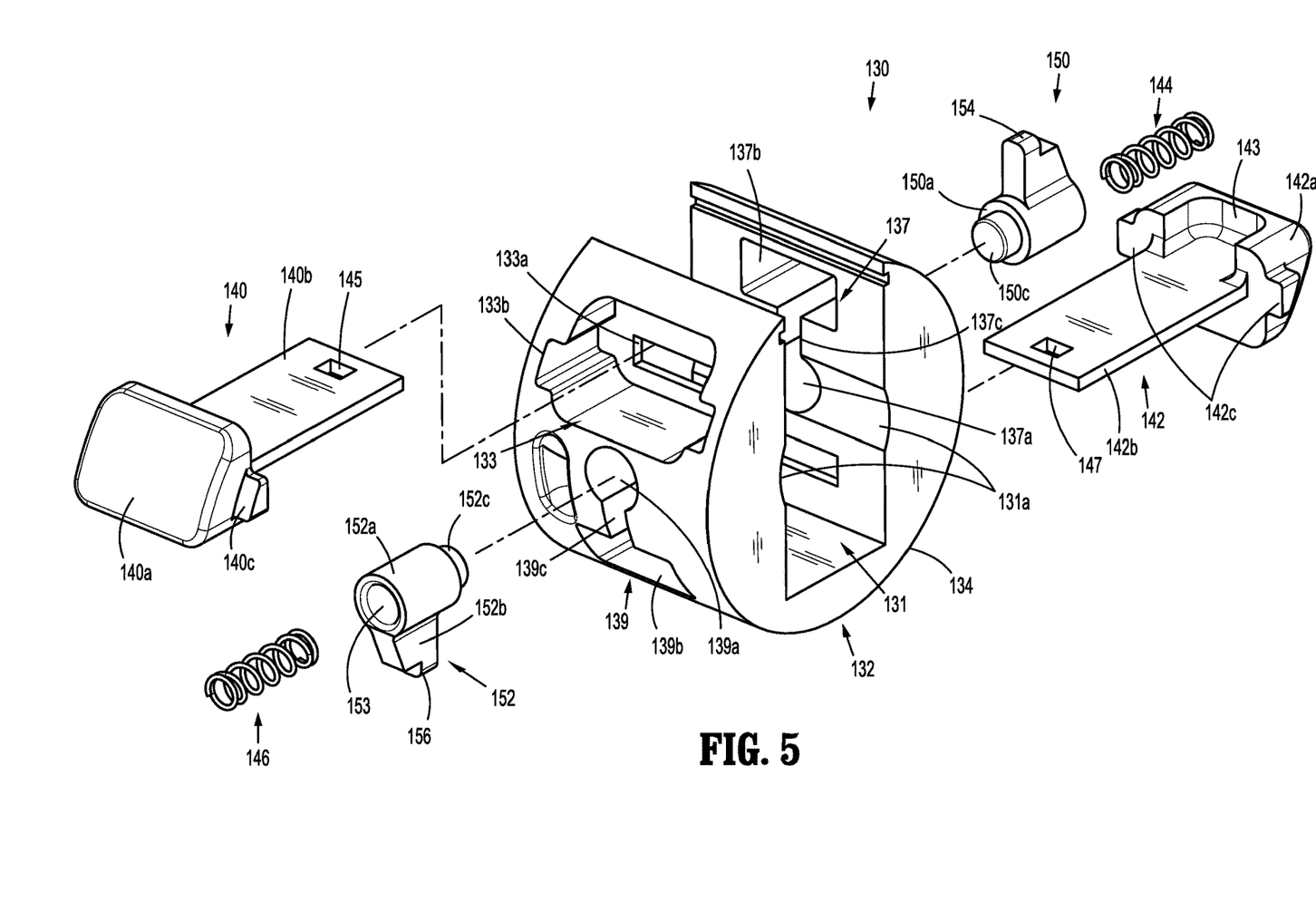
FIG. 5 is a side perspective view of the retaining mechanism shown in FIG. 3, with components separated.

With particular reference now to FIG. 5, the retaining mechanism 130 of the adapter assembly 100 includes a housing 132 supported within the outer sleeve 106 (FIG. 4) of the adapter assembly 100, first and second button members 140, 142 operably supported within the housing 132 and configured for engagement by a user, and first and second plunger members 150, 152 operably supported within the housing 132 and in engagement with the respect first and second button members 140, 142. As will be described in further detail below, first and second spring members 144, 146 are disposed within the housing 132 and bias the respective plunger members 150, 152 inward.

With continued reference to FIG. 5, the housing 132 of the retaining mechanism 130 includes a substantially cylindrical body portion 134 disposed within the outer sleeve 106 of the adapter assembly 100. The body portion 134 of the housing 132 defines a longitudinal cutout 131 for accommodating the first and second flexible bands 112a, 114a, 112b, 114b (FIG. 7) of the respective inner and outer flexible band assemblies 112, 114 of the adapter assembly 100, and for receiving the trocar assembly 120.

The body portion 134 of the housing 132 of the retaining mechanism 130 further defines first and second cutouts 133 (FIG. 5), 135 (FIG. 6) with corresponding first and second slots 133a, 135a, and corresponding first and second sets of reliefs 133b, 135b. The first and second cutouts 133, 135 operably receive respective engagement portions 140a, 142a of the first and second button member 140, 142 of the retaining mechanism 130, while the first and second slots 133a, 135a accommodate attachment portions 140b, 142b of the first and second button members 140, 142, respectively. The body portion 134 of the housing 132 further defines first and second recesses 137, 139 that accommodate the respective first and second plunger members 150, 152. The first and second recesses 137, 139 each include a cylindrical portion 137a, 139b, connected to a rectangular portion 137b, 139b by a respective channel 137c, 139c.

As noted above, the first and second button members 140, 142 of the retaining mechanism 130 each includes the engagement portion 140a, 142a, respectively, and the attachment portions 140b, 142b, respectively, extending longitudinally from the respective engagement portions 140a, 142a. The first and second button members 140, 142 further include tab portions 140c, 142c, respectively, extending laterally outwardly from the respective first and second engagement portions 140a, 142a of the respective first and second button members 140, 142.

Figure 12:
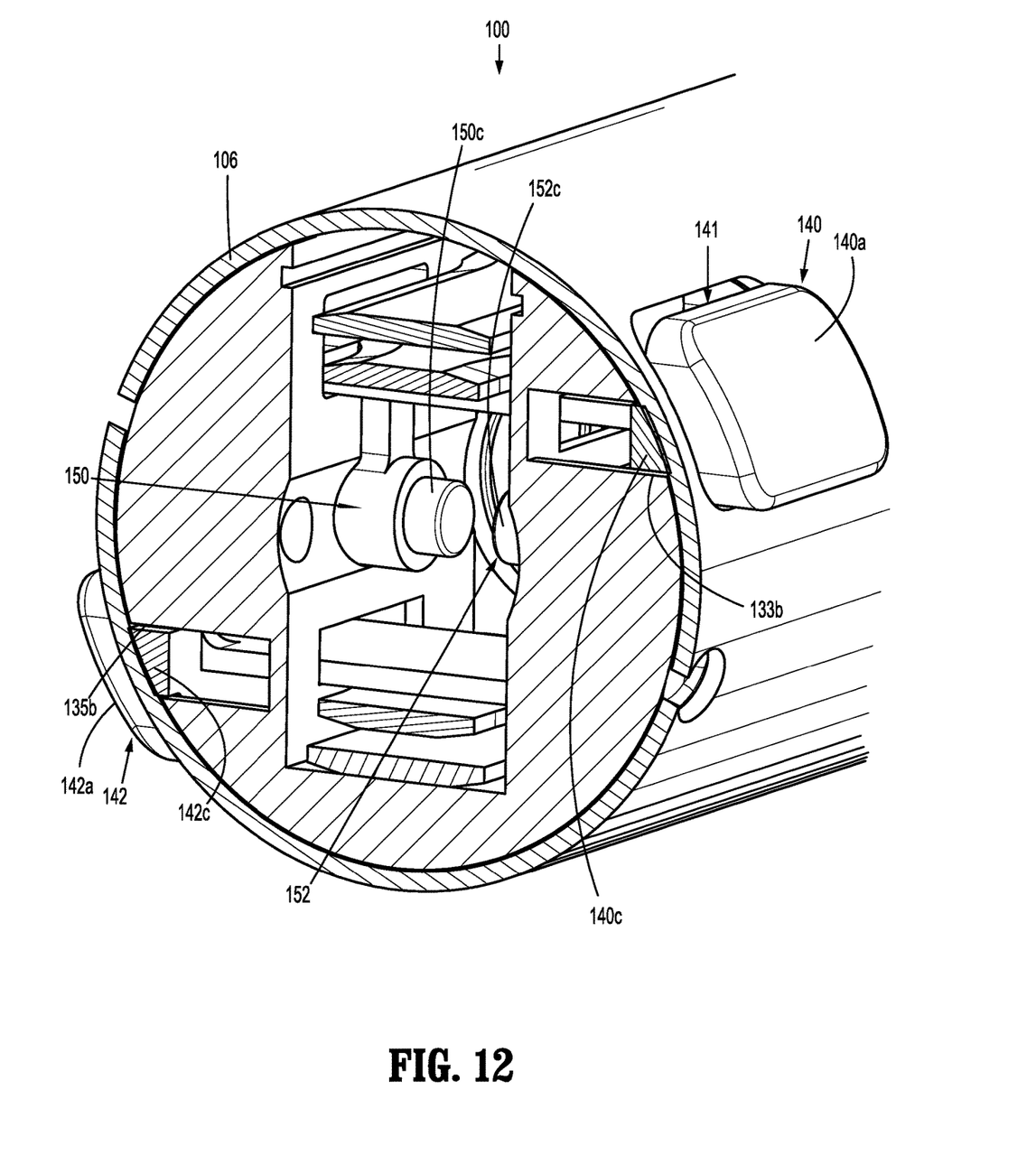
FIG. 12 is a cross-sectional end view taken along section line 12-12 shown in FIG. 10.

The engagement portions 140a, 142a of the first and second button members 140, 142 of the retaining mechanism 130 are operably received within the respective first and second cutouts 133, 135 of the housing 132 of the retaining mechanism 130 while the attachment portions 140b, 142b are slidingly received through the slots 133a, 135a (FIG. 6), respectively, corresponding to and in communication with the respective first and second cutouts 133, 135 (FIG. 12). The tab portions 140c, 142c of the respective first and second button members 140, 142 are received within the respective sets of reliefs 133b, 135b (FIG. 12) of the respective first and second cutouts 133, 135, and engage the outer sleeve 106 of the adapter assembly 100 to retain the respective first and second button members 140, 142 within the first and second cutouts 133*b*, 135*b* (FIG. 12), respectively.

The engagement portions 140*a*, 142*a* of the respective first and second button members 140, 142 of the retaining mechanism 130 each define a flush cutout 141 (FIG. 6), 143, respectively. As will be described below, the engagement portions 140*a*, 142*a* of the respective first and second button members 140, 142 extend outwardly from the outer sleeve 106 of the adapter assembly 100 when the trocar assembly 120 is removed from the adapter assembly 100 to expose the flush cutouts 141, 143 of the respective first and second button members 140, 142. The flush cutouts 141, 143 enable cleaning and sterilizing of the interior of the adapter assembly 100 without removing the retaining mechanism 130 from within the adapter assembly 100.

As noted above, the engagement portions 140*a*, 142*a* of the respective first and second button members 140, 142 of the retaining mechanism 130 are configured for operable engagement by a user. As will be detail below, engagement of the engagement portions 140*a*, 142*a* by a user to move the respective first and second button members 140, 142 inward within the first and second cutouts 133, 135, respectively, cause outward movement of the plunger members 150, 152 which permits release of the trocar assembly 120 from within the adapter assembly 100 and/or facilitates receipt of the trocar assembly 120 within adapter assembly 100.

The attachment portions 140*b*, 142*b* of the respective first and second button members 140, 142 of the retaining mechanism 130 each define an opening 145, 147 for receiving free ends 154, 156 of a flange portion 150*b*, 152*b*, respectively, of the respective first and second plunger members 150, 152. Receipt of free ends 154, 156 of the flange portions 150*b*, 152*b* of the respective first and second plunger members 150, 152 within the respective opening 145, 147 of the respective attachment portions 140*b*, 142*b* of the first and second button members 140, 142, respectively, couples the respective first and second plunger members 150, 152 to the first and second button members 140, 142, respectively, such that movement of the respective first and second button members 140, 142 causes corresponding movement of the respective first and second plunger members 150, 152.

With continued reference to FIG. 5, each of the first and second plunger members 150, 152 of the retaining mechanism 130 include a cylindrical portion 150*a*, 152*a*, respectively, the flange portion 150*b*, 152*b*, respectively, extending outwardly from the respective cylindrical portion 150*a*, 152*a*, and a locking portion 150*c*, 152*c* extending longitudinally from the cylindrical portion 150*a*, 152*a*, respectively. The first and second plunger members 150, 152 each define a recess 151, 153, respectively, for receiving at least a portion of the first and second spring members 144, 146, respectively.

The cylindrical portions 150*a*, 152*a* of the respective first and second plunger members 150, 152 of the retaining mechanism 130 are received within the respective cylindrical portions 137*a*, 139*a* of the first and second recesses 137, 139, respectively, in the housing 132 of the retaining mechanism 130. The flange portions 150*b*, 152*b* of the respective first and second plunger members 150, 152 extend through the respective channel portions 137*c*, 139*c* of the first and second recesses 137, 139, respectively, with the free ends 154, 156 of the respective flange portions 150*b*, 152*b* of the respective first and second plunger members 150, 152 received within the respective rectangular portions 137*b*, 139*b* of the first and second recesses 137, 139, respectively.

The flange portion 150*b*, 152*b* of the respective first and second plunger members 150, 152 engage the respective attachment portions 140*b*, 142*b* of the respective first and second button members 140, 142, within the respective rectangular portions 137*b*, 139*b* of the first and second recesses 137, 139, respectively.

Figure 6:
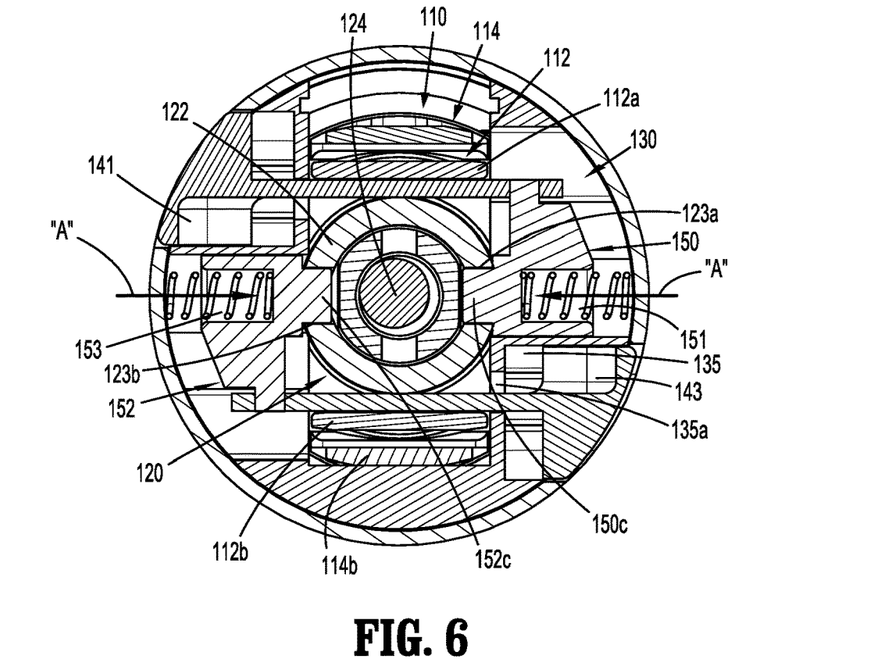
FIG. 6 is a cross-sectional end view of the adapter assembly shown in FIG. 2 taken along line 6-6, with the retainer mechanism in a lock position.

The first and second spring members 144, 146 of the retaining mechanism 130 are received within the respective recesses 151, 153 in the first and second plunger members 150, 152, respectively, and bias the respective first and second plunger members 150, 152 inwardly, as indicated by arrow "A" in FIG. 6.

Although the retaining mechanism 130 is shown as including first and second button members 150, 152, and corresponding first and second plunger members 140, 142, it is envisioned that the retaining mechanism 130 may include only one button member and only one corresponding plunger member.

Figures 10, 11:
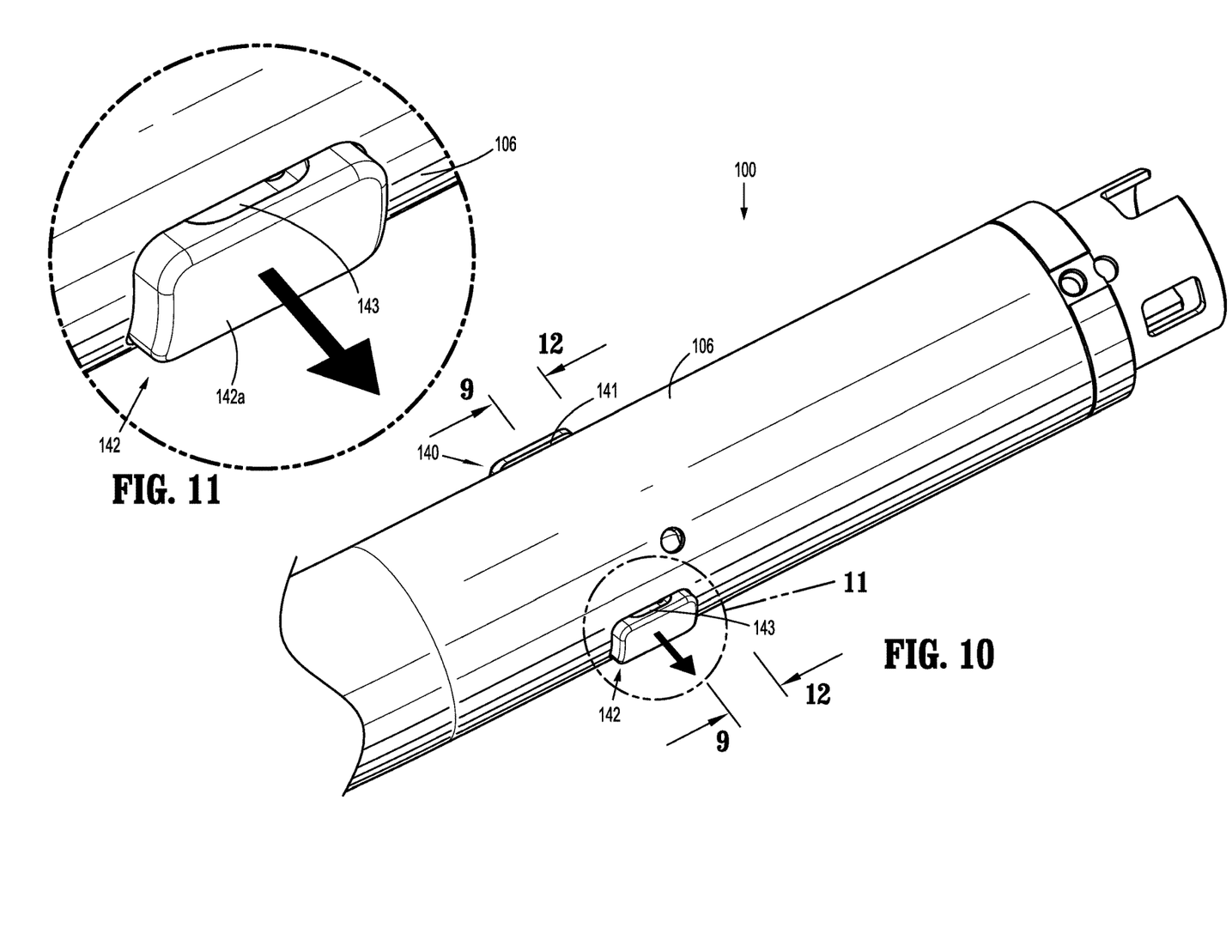
FIG. 10 is an enlarged view of the distal portion of the adapter assembly shown in FIG. 2, with the retaining mechanism in a cleanse position.
FIG. 11 is an enlarged view of the indicated area of detail shown in FIG. 10.

The first and second button members 150, 152 of the retaining mechanism 130, and the corresponding plunger members 140, 142 of the retaining mechanism 130 are movable between a first or lock position (FIG. 6), a second or release position (FIG. 7), and a third or cleanse position (FIG. 11). As will be described in further detail below, when in the lock position, the trocar assembly 120 is secured within the adapter assembly 100, while in the release position, the trocar assembly 120 may be inserted into and withdrawn from the adapter assembly 100, and in the cleanse position, the first and second button members 140, 142 extend outwardly of the sleeve 106 of the adapter assembly 100 to expose the flush ports 141, 143 of the respective first and second button members 140, 142.

With reference to FIG. 6, the first and second button members 140, 142, and the corresponding plunger members 150, 152 are shown in the lock position. In the lock position the trocar assembly 120 is fully seated within the adapter assembly 100 and is securely engaged by the retaining mechanism 130. More particularly, when in the lock position, the locking portions 150*c*, 152*c* of the respective first and second plunger members 150, 152 are received within the respective first and second openings 123*a*, 123*b* in the trocar housing 122 of the trocar assembly 120. In addition, the engagement portions 140*a*, 142*a* of the respective first and second button members 140, 142 are flush with the outer sleeve 106 of the adapter assembly 100. Maintaining the first and second button members 140, 142 flush with the outer sleeve 106 facilitates insertion of the adapter assembly 100 through an access port, lumen, and/or incision, and/or may reduce the likelihood of contaminates getting within the adapter assembly.

Figure 8:
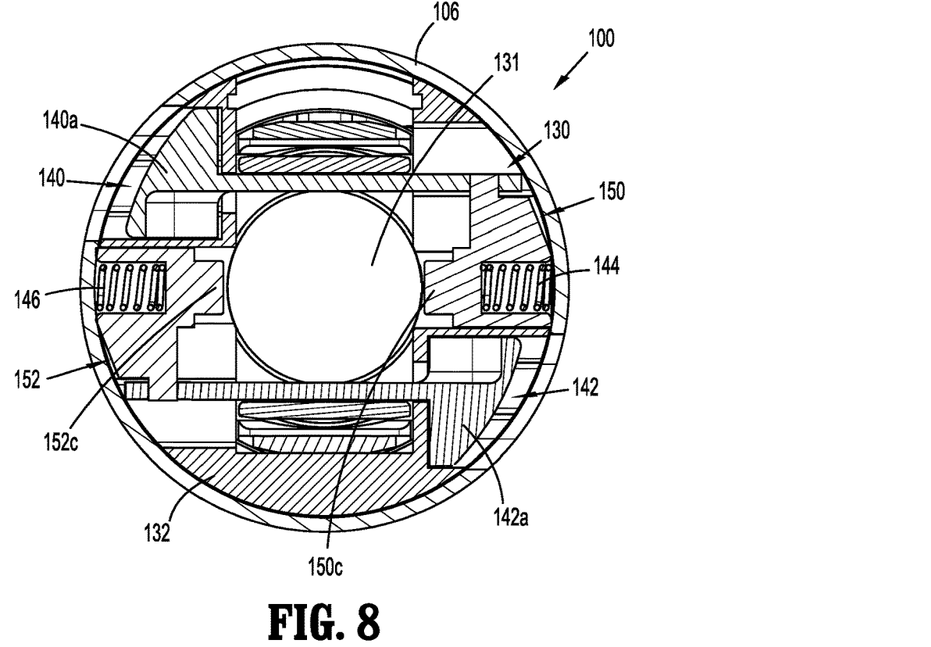
FIG. 8 is the cross-sectional end view of the adapter assembly shown in FIG. 6, with the retainer mechanism in a release position, and the trocar assembly removed.
Figure 9:
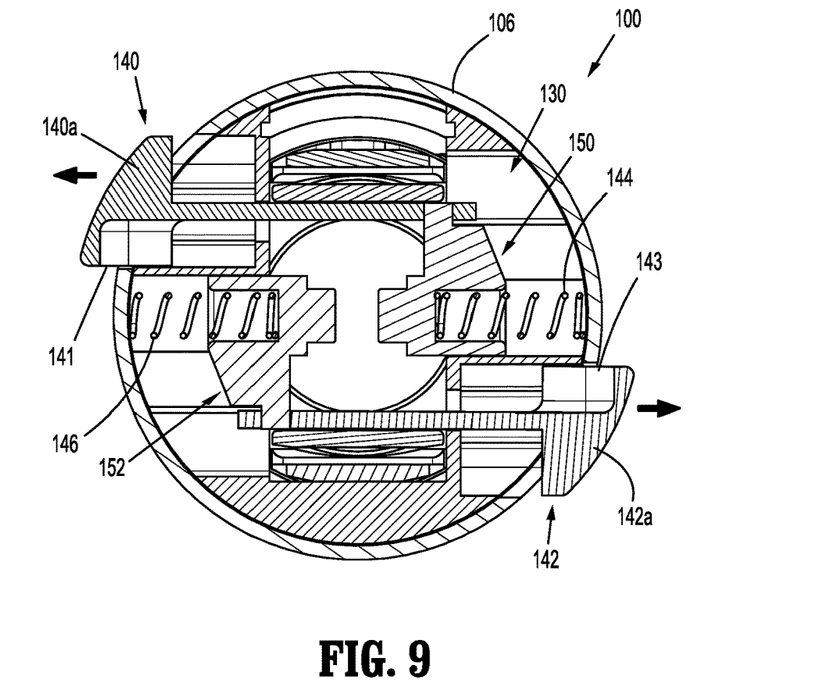
FIG. 9 is a cross-sectional end view taken along section line 9-9 shown in FIG. 10, with the retaining mechanism in a cleanse position.

Turning to FIGS. 7 and 8, the first and second button members 150, 152, and the corresponding plunger members 150, 152 are shown in the release position. In the release position, the retaining mechanism 130 (FIG. 7) is disengaged from the trocar assembly 120 so the trocar assembly 120 may be removed from within the adapter assembly 100 (FIG. 8). More particularly, the first and second button members 140, 142 of the retaining mechanism 130 are depressed, as indicated by arrows "B" in FIG. 7, to cause the respective first and second plunger members 150, 152 to move against the bias of the respective first and second spring members 144, 146, e.g., outwardly. As the first and second plunger members 150, 152 move outwardly, the flange portions 150*c*, 152*c* of the respective first and second plunger members 150, 152 withdraw from within the respective first and second openings 123*a*, 123*b* in the trocar housing 122 of the trocar assembly 120. With the first and second plunger members 150, 152 no longer engaging the trocar assembly 120, the trocar assembly 120 is removable from within the adapter assembly 100 for replacement and/or cleaning and sterilizing.

With reference now to FIGS. 9-12, the first and second button members 140, 142, and the corresponding plunger members 150, 152 of the retaining mechanism 130 are shown in the cleanse position. In the cleanse position the trocar assembly 120 is removed from the adapter assembly 100 and the first and second spring members 144, 146 bias the respective first and second plunger members 150, 152 inward. Without the trocar assembly 120 (FIG. 5) obstructing the movement of the first and second plunger members 150, 152, the first and second plunger members 150, 152 move closer together than when the first and second plunger members 150, 152 are in the lock position. In the cleanse position, the first and second button members 140, 142 are moved outwardly by the respective first and second plunger members 150, 152 beyond the outer sleeve 106 of the adapter assembly 100 by the respective first and second spring members 144, 146.

When the first and second button members 140, 142 of the retaining mechanism 130 extend beyond the outer sleeve 106 of the adapter assembly 100 the flush cutouts 141, 143 in the respective first and second button members 140, 142 are exposed to facilitate cleansing and sterilizing of the adapter assembly 100. As noted above, the tab portions 140c, 142c of the respective first and second button members 140, 142 engage an inner wall of the outer sleeve 106 of the adapter assembly 100 to maintain the respective first and second button member 140, 142 within the outer sleeve 106 of the adapter assembly 100. In this manner, the outer sleeve 106 acts as a limit stop.

The adapter assembly 100 may be provided to a clinician with the trocar assembly 120 preloaded. In the event the trocar assembly 120 is provided to the clinician separate from the adapter assembly 100, the trocar assembly 120 is loaded into the adapter assembly 100 in the reverse order of removal. In order to accommodate the trocar assembly 120 through the longitudinal passage 131 of the housing 132 of the retaining mechanism 130 the first and second button members 140, 142 are depressed, as shown in FIGS. 7 and 8, to move the first and second plunger members 150, 152, respectively, away from each other. As shown in FIG. 8, when the first and second plunger members 150, 152 are moved away from each other, the longitudinal passage 131 through the housing 132 is unobstructed, thereby allowing for receipt of the trocar assembly 120 therethrough.

Once the trocar assembly 120 is received within the adapter assembly 100, the first and second button members 140, 142 are released thereby allowing the respective first and second plunger members 150, 152 to move towards one another in response to the bias of the first and second spring members 144, 146. If the first and second openings 123a, 123b in the trocar housing 122 of the trocar assembly 120 are aligned with the flange portions 150c, 152c, respectively, of the respective first and second plunger members 150, 152 the flange portions 150c, 152c of the respective first and second plunger members 150, 152 are received within the respective first and second openings 123a, 123b and the engagement portions 140a, 142c of the respective first and second button members 140, 142 become flush with the outer sleeve 106 of the adapter assembly 100. In the event that the locking portions 150c, 152c of the respective first and second plunger members 150, 152 do not align with the respective first and second openings 123a, 123b in the trocar housing 122, the engagement portions 140a, 142a of the respective first and second button members 140, 142 remain extended beyond the outer sleeve 106, thereby indicating to the clinician that the trocar assembly is not properly seated within the adapter assembly 100.

Once the trocar assembly 120 is properly seated and secured within the adapter assembly 100, the adapter assembly 100 operates in a traditional manner.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described.

What is claimed is:

1. An adapter assembly for connecting a loading unit to a handle assembly, the adapter assembly comprising:
   an outer sleeve;
   a trocar assembly releasably securable with the outer sleeve, the trocar assembly including a trocar housing defining first and second openings; and
   a retaining mechanism configured to releasably secure the trocar assembly within the outer sleeve, the retaining mechanism including first and second button members configured for operable engagement by a user, the first and second button members are movable between a lock position with the first and second button members being flush with an outer surface of the outer sleeve, a release position in which the first and second button members are recessed below the outer surface of the outer sleeve, and a cleanse position in which the first and second button members extend beyond the outer surface of the outer sleeve, each of the first and second button members defining a cutout that is exposed when the first or second button member is in the cleanse position, the trocar assembly securely coupled within the outer sleeve in the lock position.

2. The adapter assembly of claim 1, wherein the retaining mechanism further includes first and second plunger members in operable engagement with the respective first and second button members such that movement of the first button member results in corresponding movement of the first plunger member and movement of the second button member results in corresponding movement of the second plunger member.

3. The adapter assembly of claim 2, wherein each of the first and second plunger members includes a flange portion configured for selective reception within the respective first and second openings of the trocar housing.

4. The adapter assembly of claim 2, wherein the retaining mechanism further includes first and second spring members for biasing the respective first and second plunger members towards each other.

5. The adapter assembly of claim 2, wherein the first and second plunger members are spaced apart when the first and second button members are in the lock position.

6. The adapter assembly of claim 2, wherein the first and second plunger members engage the trocar housing when the first and second button members are in the lock position.

7. The adapter assembly of claim 2, wherein the first and second plunger members are spaced from the trocar assembly when the first and second button members are in the release position.

8. The adapter assembly of claim 1, wherein each of the first and second button members includes a pair of tab portions, the tab portions being configured to engage the outer sleeve to retain the first and second button members within the adapter assembly.

9. The adapter assembly of claim 1, further including a connector housing for releasably securing a loading unit to the outer sleeve.

10. The adapter assembly of claim 1, wherein the trocar assembly includes a trocar member selectively extendable from the trocar housing.

11. An adapter assembly for connecting a loading unit to a handle assembly, the adapter assembly comprising:
an outer sleeve;
a trocar assembly releasably securable with the outer sleeve, the trocar assembly including a trocar housing defining first and second openings; and
a retaining mechanism configured to releasably secure the trocar assembly within the outer sleeve, the retaining mechanism including first and second button members configured for operable engagement by a user, the first and second button members are movable between a lock position with the first and second button members being flush with an outer surface of the outer sleeve, a release position in which the first and second button members are recessed below the outer surface of the outer sleeve, and a cleanse position in which the first and second button members extend beyond the outer surface of the outer sleeve, each of the first and second button members including at least one tab portion that engages the outer sleeve when the respective first or second button member is in the cleanse position, the trocar assembly securely coupled within the outer sleeve in the lock position.

12. The adapter assembly of claim 11, wherein the retaining mechanism further includes first and second plunger members in operable engagement with the respective first and second button members such that movement of the first button member results in corresponding movement of the first plunger member and movement of the second button member results in corresponding movement of the second plunger member.

13. The adapter assembly of claim 12, wherein each of the first and second plunger members includes a flange portion configured for selective reception within the respective first and second openings of the trocar housing.

14. The adapter assembly of claim 12, wherein the retaining mechanism further includes first and second spring members for biasing the respective first and second plunger members towards each other.

15. The adapter assembly of claim 12, wherein the first and second plunger members are spaced apart when the first and second button members are in the lock position.

16. The adapter assembly of claim 12, wherein the first and second plunger members engage the trocar housing when the first and second button members are in the lock position.

17. The adapter assembly of claim 12, wherein the first and second plunger members are spaced from the trocar assembly when the first and second button members are in the release position.

18. The adapter assembly of claim 11, wherein each of the at least one tab portions includes a pair of tab portions.

19. The adapter assembly of claim 11, further including a connector housing for releasably securing a loading unit to the outer sleeve.

20. The adapter assembly of claim 11, wherein the trocar assembly includes a trocar member selectively extendable from the trocar housing.

* * * * *